United States Patent [19]
Charm et al.

[11] Patent Number: 5,389,335
[45] Date of Patent: Feb. 14, 1995

[54] HIGH TEMPERATURE, SHORT TIME MICROWAVE HEATING SYSTEM AND METHOD OF HEATING HEAT-SENSITIVE MATERIAL

[75] Inventors: Stanley E. Charm, Boston; Steven Landau, Brookline; Hossein Zarrineghbal, Winchester; Robert F. Golden, Acton, all of Mass.

[73] Assignee: Charm Sciences, Inc., Malden, Mass.

[21] Appl. No.: 79,680

[22] Filed: Jun. 18, 1993

[51] Int. Cl.6 .............................................. M61L 2/00
[52] U.S. Cl. .................................... 422/21; 165/65; 422/307; 426/241; 426/521; 426/522; 435/2
[58] Field of Search .................... 422/21, 307; 435/2; 426/241, 243, 521, 522; 219/10.55 R, 10.55 A, 10.55 F, 10.55 M; 210/748, 764, 224, 177, 181, 182, 96.2, 929; 165/65; 34/259, 264

[56] References Cited

U.S. PATENT DOCUMENTS

| | | | |
|---|---|---|---|
| Re. 30,780 | 10/1981 | Stenstrom | 422/21 X |
| 3,706,631 | 12/1972 | Falk | 422/21 |
| 4,614,514 | 9/1986 | Carr et al. | 422/21 X |
| 4,839,142 | 6/1989 | Charm | 422/21 |
| 4,975,246 | 12/1990 | Charm | 422/21 |
| 5,260,019 | 11/1993 | Petersen | 422/21 |
| 5,288,471 | 2/1994 | Corner | 422/307 |

*Primary Examiner*—Robert J. Warden
*Assistant Examiner*—Krisanne M. Thornton
*Attorney, Agent, or Firm*—Richard P. Crowley

[57] ABSTRACT

A high temperature, short time microwave heating system 10 for heat-sensitive liquid material to inactivate or reduce pathogenic agents or organisms, such as viral contaminants. The system 10 includes a disposable cartridge 26 consisting of a preheater 32, a microwave heating coil 56 and cooler 58 with the heating coil 56 adapted to be easily inserted in and removed from the microwave heating field.

34 Claims, 3 Drawing Sheets

HIGH TEMPERATURE, SHORT TIME MICROWAVE HEATING SYSTEM AND METHOD OF HEATING HEAT-SENSITIVE MATERIAL

BACKGROUND OF THE INVENTION

It is desirable to sterilize, pasteurize or otherwise heat treat heat-sensitive material by heating such heat-sensitive material, such as biological fluids, to high temperatures for very short time periods without effecting substantially the other desirable properties of the heat-sensitive material. U.S. Pat. No. 4,839,142, issued Jun. 13, 1989 and U.S. Pat. No. 4,975,246, issued Dec. 4, 1990, both disclose high temperature, short time heating systems and methods for the heating of heat-sensitive material to destroy substantially the pathogenic or other microorganisms, such as viruses, in the heat-sensitive material without substantially effecting other desirable properties of the heat-sensitive material, such as proteinaceous matter.

These patents disclose a system and method in which heat-sensitive material, such as a biological fluid, such as blood plasma or serum or tissue culture or tissue-type or other material, is rapidly heated by microwave energy to a selected temperature, held for a very short holding time and then rapidly cooled and then recovered. Typically, the method described provides for rapidly heating the heat-sensitive material at a rate of over 50° C. per second, for example 50° C. to 2000° C. per second, for a heating time period typically less than one second to a preselected temperature of typically over about 60° C. and to a temperature wherein the rate of reduction or destruction of the pathogenic organisms is greater than the rate of destruction of the heat-sensitive material by employing microwave energy to accomplish the rapid heating. The method includes holding the heated heat-sensitive material at a preselected temperature for a short holding time period which might be quite short, for example less than 0.05 seconds, and then rapidly cooling the heated heat-sensitive material to a preselected lower temperature, typically less than about 40° C., or typically less than 30° C., in a short time period to provide a cooled heat-sensitive material with the virus or agent destroyed or reduced. The heat-sensitive material is rapidly heated and rapidly cooled, while circulating the heat-sensitive material through a plastic tubing, with the total heating, holding and cooling time periods not greater than 1.0 seconds and sufficiently short so as not to substantially effect the desirable properties, such as the Factor VIII and IX properties of blood plasma or serum, but sufficient for the desirable reduction of the pathogenic organisms, viruses or microorganisms in the heat-sensitive material, typically to effect a multilog, e.g. six-log or more, cycle reduction of the microorganism.

It is desirable to provide for a new, efficient, controlled batch and continuous system and method for the high temperature, short time heating for heat-sensitive material which overcomes at least some of the disadvantages in the prior high temperature, short time heating system and method.

SUMMARY OF THE INVENTION

The invention relates to a high temperature, short time heating system and method and in particular, to a high temperature, short time heating system and method for heat-sensitive material which will preserve the selected biological characteristics of the heat-sensitive material, while achieving multilog reductions of pathogenic agents, such as viruses, in the heat-sensitive material.

The high temperature, short time heating system of the invention is directed to heat-sensitive material, particularly biological fluids, which system comprises a microwave wave guide to provide microwave energy to the heat-sensitive fluid, typically a liquid, to be treated, and microwave power supply to supply electrical power to the microwave wave guide. The system includes computer and electronic controls optionally with a display screen and optionally with a printer to provide for control of the process parameters of the high temperature, short time heating system, such as the preheating, heating and cooling times and temperatures of the heat-sensitive material. The system includes a pump or pump means to pump the heat-sensitive fluid through the system and a feed source, or feed container, for the heat-sensitive fluid to be treated, and a collection source for the collection of the sterilized, pasteurized or heat-treated fluid after passing through the system.

The system also includes a cartridge, typically in the preferred embodiment, a disposable, easily inserted and removable cartridge which provides a movable sanitary system with disposable contact parts for simple cleaning and sterilization, particularly for use with blood plasma, serum and with tissue cultures and other sanitary, sensitive-type material. The cartridge includes a preheater composed of a housing and containing a plurality of tubing in the housing for the passage of the fluid to be preheated and treated therethrough, and an inlet and an outlet for the introduction and withdrawal of hot water to provide for preheating of the fluid in the tubing. The cartridge would also include a microwave heating coil containing a plastic or non-microwave susceptible material holder and plastic tubing susceptible to the passage of microwave energy, such as flexible, transparent plastic tubing, to permit the rapid microwave heating of the preheated fluid passing through the tubing, the microwave heating coil positioned to form uniform generally parallel loops and positioned within the microwave field of the microwave guide and adapted to be inserted within an opening in the microwave guide and into the microwave heating field.

The cartridge includes a cooler containing a housing with a plurality of coils of tubing to receive the microwave heated fluid and an inlet and outlet for the introduction and withdrawal of cold water in the housing to cool rapidly the microwave heated fluid to a temperature generally less than 40° C. in a time less than about 1.0 second, and preferably less than about 0.5 seconds. The cartridge typically would include metal tubing in the preheater and the cooler, such as stainless steel tubing, and include flexible, microwave transparent plastic tubing, such as a fluorocarbon tubing, like Teflon ® tubing, typically transparent, connected to the metal tubing of the preheater and between the outlet of the preheater and the inlet of the cooler and with other tubing means to connect the feed source, the pump, the cartridge and the collection means to permit the pumped passage of the fluids from the feed source by the pump through the cartridge means and into the collection means.

The cooler may be mounted on a bracket which is in turn mounted to an adjustable screw. As the screw is adjusted the cooler moves up or down, drawing an amount of tubing out of the microwave field. The portion of the tubing between the microwave field and the cooler holds the microwave heated fluid at a relatively constant temperature for a period of time (the hold time) prior to cooling. The hold time is proportional to the velocity of the fluid in the tubing and the length of the tube between the microwave field and the cooler. By adjusting the length of this tubing the hold time can be adjusted without changing the flow rate of the heat sensitive fluid.

The microwave heating coil used comprises a plurality of loops of the plastic tubing of defined length within a plastic coil retaining holder means to retain the plastic tubing in a generally parallel, uniform, side by side, slightly spaced apart, coiled arrangement of the plastic tubing which may be easily positioned within the microwave guide. The plastic coil retainer or holder may comprise a base portion and a downwardly extending holder of a plastic material adapted to extend through an opening in the microwave guide housing and into the microwave heating field and having a plurality of spaced apart, side by side slots or holes through which the microwave plastic tubing may be threaded, and generally with a plurality of aligned upper and lower holes to thread the tubing therefrom and to hold the plastic tubing in the arranged, coiled manner. The cartridge with the preheater, the microwave coil and the cooler should generally be arranged in one preferred embodiment so that the entire unit may be disposable, and typically would comprise a base with the preheater and the cooler on the upper surface of the base and the microwave heating coil extending below the base for use in the microwave guide energy field. The employment of a disposable cartridge is particularly preferred and adaptable with culture media, plasma material or other type material which where the cartridge must be cleaned between each use.

The microwave heating coil may be mounted on a fixed frame or a rotatable grooved spindle. When the cooler is adjusted, sufficient slack tubing is provided to allow the cooler to pull out the required length of tubing when adjusted. If the tubing is mounted on a rotatable spindle, when the cooler is adjusted the spindle rotates thus feeding tubing to the cooler and drawing tubing from slack supplied between the preheater and the microwave field.

Generally, the disposable cartridge employed in sterilizing or pasteurization operations comprises a combination of a preheater-type heat exchanger, a coiled microwave tube and a cooling heat exchanger with a continuous tube constructed of lengths of metal and plastic material passing through the cartridge, the metal tubing material being used in the preheater and the cooler, while the plastic tubing material is used in the microwave coil guide. In operation, the heat-sensitive fluids are passed through this tubing which runs through the preheater, the microwave field and the cooler, with the flexible plastic tube of defined length and diameter and coiled in the microwave coil guide to provide satisfactory exposure to the microwave energy and to raise rapidly, e.g., less than 200 milliseconds, the heat-sensitive fluid to the high appropriate temperatures, e.g. over 60° C., such as 70° C. to 180° C., within the short time period desired, e.g. 5 milliseconds. The tube diameter, the length and the number of coils in the microwave field, may be varied as desired.

The computer electronic control employed in the process merely operates on an algorithm for the control of the process for microwave sterilizing, pasteurizing or otherwise heat-treating the heat-sensitive fluid, and which accepts real time inputs from pressure, flow, temperature, motor and other sensors in the system and employs this information to control the time-temperature history of the heat-sensitive fluid flowing through the flexible plastic tubing which is coiled through the microwave field.

The system optionally and preferably includes the accurate sensing of the fluid temperature in the inlet and outlet of the microwave coiled plastic tubing and in particular, employs with transparent tubing a non-invasive IR infrared sensor employing an IR sensor in conjunction with fiber optic cable in which an infrared sensor or fiber optic cable is coupled to an IR sensor placed in physical contact with and adjacent to the microwave plastic tube in which the heat-sensitive material is flowing in and out of the microwave coil. Generally, the signal from the IR sensors is amplified and then sent into the computer electronic control to act as one of the process parameters.

The system of the invention may be used with a wide variety of fluids to be sterilized, pasteurized or heat treated, which would include heat-sensitive liquids, such as biological liquids, solutions, suspensions and the like, and would include, but not be limited to, blood and serum, plasma, cell culture media and the like, and in particular, heat-sensitive material which contains HIV (human immunodeficiency virus), EMC (encephalo myocardia virus) and unknown viruses which can cause a major problem in such a heat-sensitive material. The system permits viral inactivation of a heat-sensitive material either in batch form or in a continuous operation. The system avoids the difficulties associated with other systems and methods, for example, conventional thermal methods which tend to destroy delicate biological materials and the use of filters which clog with cell culture media or blood products, or conventional chemical methods which add substances are difficult to remove or otherwise effect the fluid.

The system permits the high temperature, short time heating of fluid, for example in less than 0.1 seconds, for example, less than 0.05 seconds, such as 0.01 seconds. The system permits a total heating, holding, and cooling time of less than about 1 second, with heating and cooling total times of only a few milliseconds, typically 500 to 200 milliseconds or less.

The invention will be described for the purposes of illustration only in connection with certain embodiments; however, it is recognized that various changes, additions and improvements can be made in the invention by those persons skilled in the art, all falling within the spirit and scope of the invention.

DESCRIPTION OF THE EMBODIMENTS

Figure 1:
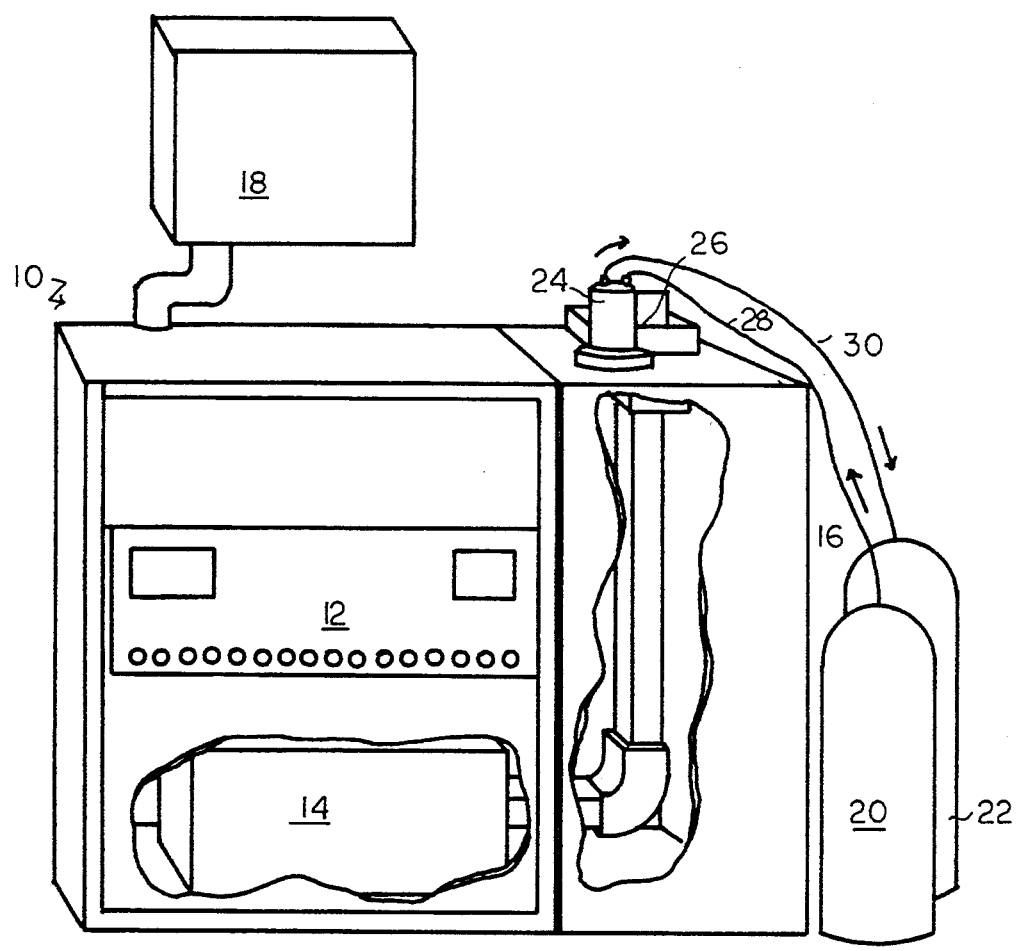
FIG. 1 is perspective view of the high temperature, short time microwave heating and cooling system of the invention.

FIG. 1 shows the high temperature, short time microwave heating system 10 of the invention which comprises computer electronics controls 12 to monitor the parameters of the high temperature, short time process which includes a computer display 18 and which system includes a microwave power supply 14 which supplies microwave power to microwave guide 16. The system includes a feed tank 20 to supply a heat-sensitive material to be treated and a collection tank 22 for the recovery of the sterilized, viral inactivated or heat processed heat-sensitive material and which includes a pump 24 connected through tubing 28 and 30 and a disposable cartridge 26, the disposable cartridge shown in more detail in FIG. 2, and which is disposably placed over and within an opening at the end of the wave guide 16, so that the portion of the disposable cartridge 26 comprising the microwave coil is disposed in the microwave energy field.

Figure 2:
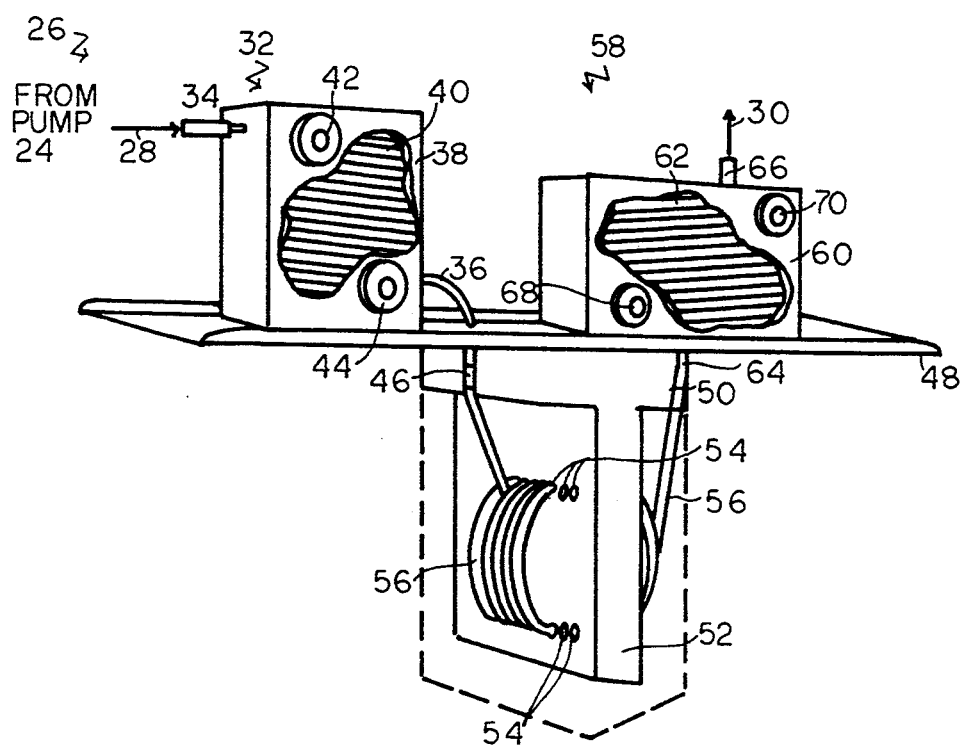
FIG. 2 is a perspective, schematic, enlarged illustration of the disposable cartridge system used in the system of FIG. 1.

FIG. 2 is a perspective view of a disposable cartridge 26 for use with the system 10 in FIG. 1 which cartridge has a preheater 32 containing a inlet 34 for the introduction of a heat-sensitive material from a pump 24 to be treated, the preheater comprising a transparent plastic housing 38 containing a plurality of coils of stainless steel metal 40 therein and having an outlet 36 which connects to a metal or plastic tubing 46 connection wherein the housing 38 has an inlet 42 for the introduction of hot water, for example, 70° C. to 95° C., and more particularly 80° C. to 85° C., and an outlet 44 for the withdrawal of the hot water after preheating the heat-sensitive fluid in the coil 40.

The disposable cartridge 26 includes a plastic, T-shaped microwave coil holder having a base 50 and a downwardly extending portion 52, the base extending to and secured to the bottom of a base 48 on which the preheater 32 and a cooler 58 are positioned, the base 50 being rectangular and adapted to fit into the opening at the end of the microwave guide 16. The holder extension 52 includes a plurality of spaced apart, aligned holes 54 in the upper and lower sections of the holder and includes a plastic tubing 56, such as, but not limited to, a Teflon ® tubing, of a desired diameter, such as 1/16 to ½ inch, sequentially wound or threaded through the holes 54 to form a plurality of side-by-side, generally uniform, spaced apart coils which are to be placed in the microwave field, the diameter of the tubing and the number of coils with the pumping rate selected to provide for the desired exposures and for the rapid heating of the heat-sensitive material within the coils 56. The plastic coil 56 is secured by being threadably turned onto threads at the end of the stainless steel outlet 46 from the preheater 32.

The disposable cartridge 26 also includes on the upper portion of the base 48 a cooler 58 which comprises a transparent plastic housing 60 having a plurality of coils of stainless steel tubing 62 therein and having an inlet 64 which is threadably connected to the plastic tubing 56 from the microwave coil 50, and an outlet 66 in the transparent housing 60 which includes an inlet 68 for the introduction of cold water, and an outlet 70 for the withdrawal of cold water, the cold water being typically less than 10° C., for example, 2° C. to 10° C., where the total system is arranged, for example, for 100 liters per hour of treatment of a heat-sensitive fluid, and the outlet tubing also selected so as to provide for a flow rate of 100 milliliters per second of heating and cooling the water. The flexible plastic tubing 56 employed in the microwave cooling guide may vary in length and diameter and in composition, but may comprise Teflon ®, polyethylene, PVC or other tubing. However, it is preferable that the tubing be transparent, particularly when employed with the optical fiber IR sensor temperature system. The disposable cartridge 26 as designed and shown in FIG. 2 is designed to be inexpensive and disposable, so that the need for cleaning and sterilization of the tubing after each use is dispensed with and which is particularly useful for the treatment of blood plasma and serum or tissue cultures.

Figure 3:
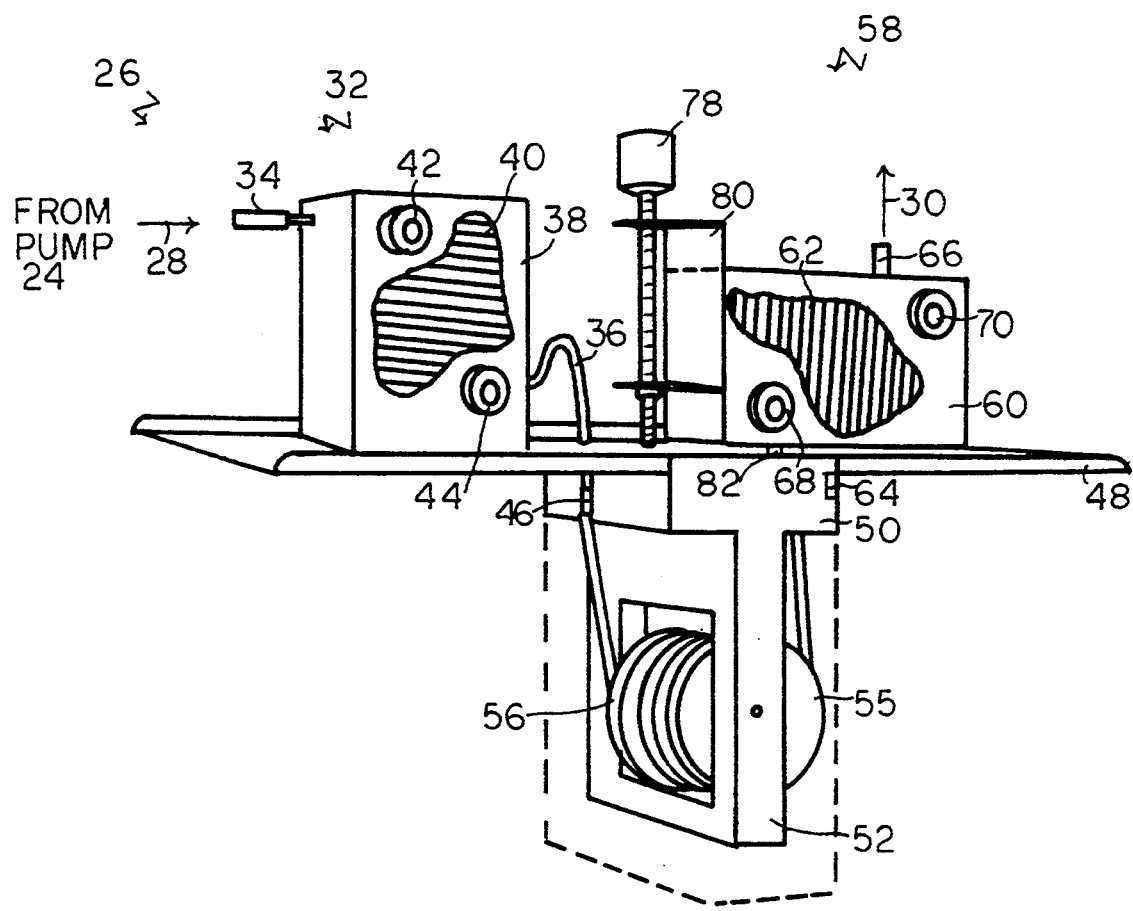
FIG. 3 is a perspective, schematic illustration of an alternative disposable cartridge system used in the system of FIG. 1.

FIG. 3 is a perspective of an alternative disposable cartridge 26 for use with the system 10 in FIG. 1 which cartridge consists of a preheater 32 containing an inlet 34 for the introduction of a heat-sensitive material from a pump 24, the preheater comprising a transparent plastic housing 38 containing a plurality of coils of stainless steel metal tubing 40 therein which connects to plastic tubing 36 which has sufficient length or slack to allow adjustment of the cooler 58 and is supported to facilitate movement in and out of the microwave field. The housing 38 has an inlet 42 for the introduction of hot water or other fluids, for example 50° C. to 100° C., and more particularly 80° C. to 85° C., and an outlet 44 for the withdrawal of the hot water after preheating the heat sensitive fluid in the coil 40.

The disposable cartridge 26 in FIG. 3 includes a plastic frame extension 52 which holds a plastic spindle coil holder 55 grooved to hold the coils in the desired spacing. The frame 52 has a base 50 extending to and secured to the bottom of a base 48 on which the preheater 32 and a cooler 58 are positioned, the base being rectangular and adapted to fit into the opening at the end of the microwave guide 16. The spindle coil holder 55 holds sequential coils of plastic tubing and can turn in the frame 52 when the cooler 58 is adjusted with the cooler adjustment screw 78. The spindle 54 holds the tubing coil 56 such as, but not limited to, a Teflon ® tubing, of a desired diameter, such as 1/16 to ½ inch, sequentially wound on the spindle 55 to form a plurality of side-by-side, generally uniform, spaced apart coils which are to be placed in the microwave field, the diameter of the tubing and the number of coils with the pumping and cooler adjustment are selected to provide for the desired exposures and for the rapid heating of the heat-sensitive material within the coils 56. The plastic coil 56 is secured by being wound into threads at the end of the stainless steel coil 40 in the preheater 32.

The disposable cartridge 26 in FIG. 3 also includes on the upper portion of the base 48 a cooler 58 which comprises a transparent plastic housing 60, mounted on a bracket 80 which can be adjusted up or down using screw 78 thus extending the length of plastic tubing 82 outside of the microwave field and prior to the cooler which determines the time at which the heat sensitive fluid is held at the desired temperature and having a plurality of coils of stainless steel tubing 62 therein and having an inlet 64 which is threadably connected to the end of the plastic tubing 56 making up the microwave coil, and an outlet 66 in the transparent housing 60 which includes an inlet 68 for the introduction of cold water or other coolant, and an outlet 70 for the withdrawal of cold water or coolant, the cold water being typically less than 10° C., for example, 2° C. to 10° C., where the total system is arranged for example for 100 liters per hour of treatment of a heat sensitive fluid, and the outlet tubing also selected so as to provide for a flow rate of 100 milliliters per second of preheating fluid and coolant.

In operation, the disposable cartridge 26 (as in FIG. 2 or 3) is used by merely inserting the base 50 and extension holder 52 with the coiled up tubing 56 into the top rectangular open space of the housing of the microwave guide 16 in system 10, so that the base 48 rests on the top portion of the system 10 of the housing of the wave guide while the extensions 50 and 52 with tubing 56 is then placed in the microwave energy field of the wave guide 16. If an adjustable cartridge such as that in FIG. 3 is used, the screw 78 (FIG. 3) is then adjusted to achieve the desired hold time. The tubing 28 is then connected to the inlet 34 and the tubing 30 connected to the outlet 66. After the sterilizing, pasteurizing or heat treatment of the heat-sensitive fluid, the disposable cartridge 26 may then be disconnected and lifted out and discarded, and a new cartridge 26 then inserted in the opening at the top of the wave guide 16 of the system 10.

Figure 4:
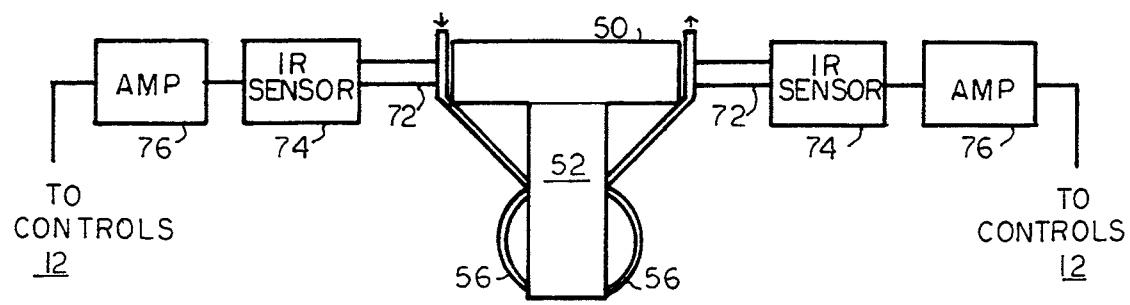
FIG. 4 is a schematic illustration of the infrared fiber optic, temperature sensing system used with the microwave heating coil-shown in FIG. 2

FIG. 4 is a schematic plan view of the infrared fiber optic temperature sensor, a portion of the system 10. The IR temperature sensor system is adapted for use wherein the tubing 56 is transparent and provides for a non-invasive technique for the accurate measurement of the inlet and outlet temperature into the microwave heating coil 56, which includes as illustrated a plurality of optical glass fibers placed together within an outer cable form 72 with the end of the optical fibers adjacent the outer transparent surface 56 on the inlet and outlet side of the microwave heating coil 56 and with the fibers adapted to collect and forward to an infrared sensor 74 the infrared heat of the fluid flowing in the tubing 56 to be converted into a temperature signal and the electrical signal amplified by an amplifier 76 and then returned to controls 12 contained in the monitoring system 10.

The IR sensor 74, in conjunction with the optical fiber 72, provides for an accurate, non-invasive technique for accurate measurement of the temperature of the heat-sensitive fluid at the inlet and outlet of the coil 56. In one embodiment, the tubing 56 would comprise a Teflon ® tubing of ⅛ inch outside diameter and 1/16 inch inside diameter and is of an IR transparent material. The standard optical fibers for example may be made of zirconium fluoride glass having a diameter of about 100 microns and wherein the fibers may be arranged in multiple rows, such as two parallel rows to the tubing 56 against which they are placed. The number of optical fibers to be used may vary, but generally from 10 to 100 fibers, e.g. 20 to 50, would typically be employed with the fiber optic fibers placed within a fiber optic cable 72 terminated with a standard SMA connector, and then thereafter coupled with any brand of an IR sensor 74 and amplified. The IR sensor, for example, may be, but is not limited to, the Williamson Fiber View 6000, fiber optics single wave length, 4-wire, non-contact temperature transmitter and control system manufactured by Williamson Corporation of Concord, Mass., or similar infrared control system.

Generally, the selection of IR sensor may differ depending upon the inlet or outlet temperature, the IR sensor typically being a broad band of 1-4 microns and selected, for example, to measure the inlet temperature to the tubing 56, which would be from 45° C. to 65° C., and the outlet temperature ranging from about 70° C. to 110° C. The end of the fiber optics is placed adjacent to the wall of the transparent tubing 56 and should be small enough to have an acceptable angle of acceptance in contact with the wall of the tubing 56.

Figure 5:
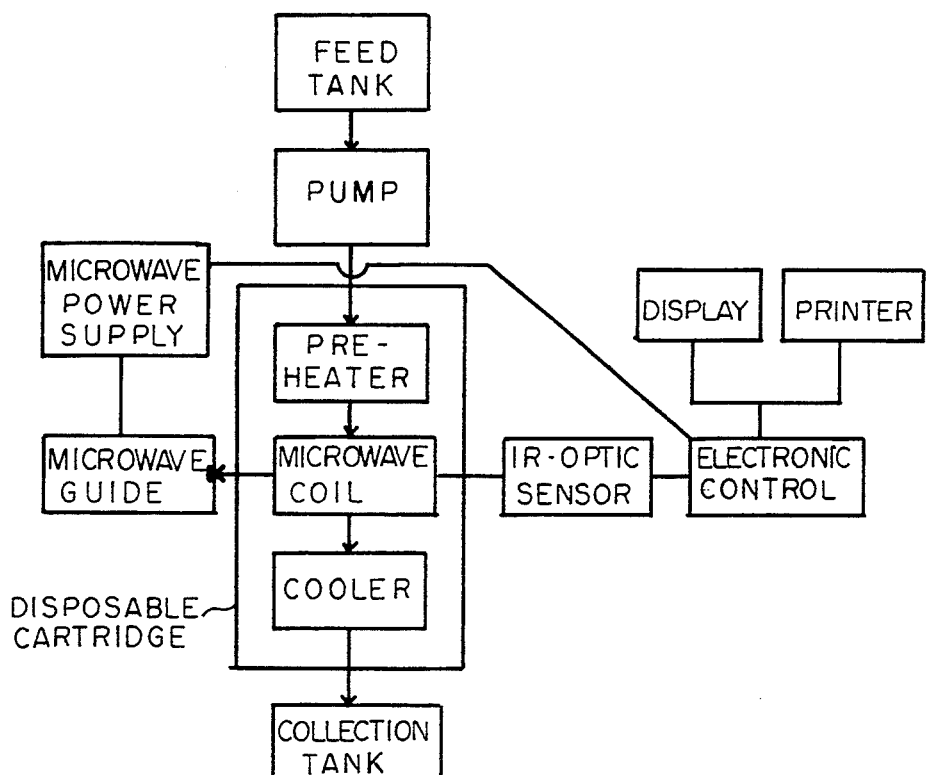
FIG. 5 is a schematic illustration of a block flow diagram of the components of the system of the invention.

FIG. 5 is a block-flow schematic diagram illustrating the system 10 of FIG. 1 in block-flow form.

Figure 6:
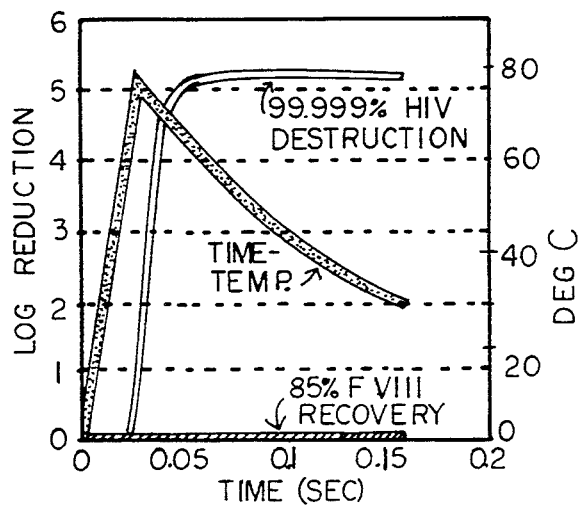
FIG. 6 is a graphical illustration of a high temperature, short time example of the viral inactivation of HIV in a blood plasma employing the system of FIG. 1 and recovering a heat-sensitive material Factor VIII using the system of FIG. 1.

FIG. 6 is a graphical illustration of an example of viral inactivation of HIV virus in blood plasma and recovery of the heat-sensitive viral inactive blood plasma employing the system 10 of the invention wherein the heat-sensitive material comprises a blood plasma and wherein the length of the tubing in the preheater 40 is about four feet and the length of the tubing in cooler 62 is about four feet, and wherein ⅛ inch Teflon ® tubing 56 employed is about two feet in length and the holder 52 with the preheat inlet temperature to the microwave heating coil is 50° C. The graphical illustration shows an abscissa set forth in time (seconds) and an ordinate both in log reduction and degrees Centigrade and illustrates the rapid heating of the blood plasma to about 75° C. and the rapid cooling in a timed period of 0.02 seconds and a rapid cooling of about 0.2 seconds to a low temperature of 30° C. and the substantial destruction of 99.999% of the HIV virus with a recovery of the blood plasma of 85% of the F-VIII factor.

The described and illustrated system for the high temperature, short time heating of a material permits batch and continuous operation and employs preferably a disposable cartridge for use with materials which require a sanitary-type system and thus avoids frequent cleaning and sterilization, and yet, the system preserves the biological characteristics of the heat-sensitive material while achieving multilog reductions in pathogenic organisms.

What is claimed is:

1. A high temperature, short time microwave system for the heating, holding and cooling of a heat-sensitive fluid for the reduction or inactivation of organisms therein to provide a heat-treated cool fluid, and which system comprises in combination:
   a) a housing having a microwave guide means to provide a microwave energy field to heat the fluid to be treated in the system and having an opening in one end of the housing;
   b) a microwave power supply to supply microwave power to the microwave guide means;
   c) feed source means for providing a source of heat-sensitive fluid to be treated;
   d) electronic control means to provide for the control of heating, holding and cooling times and temperatures of the fluid in the system;
   e) pump means to pump the fluid through the system;
   f) collection means for the collection of the heat-treated cooled fluid;
   g) cartridge means which comprises in combination:
      i) a preheater means on a base containing tubing therein for the passage of the fluid to be treated from the feed source means and means to permit the fluid passing within the tubing to be preheated to a preselected temperature;

ii) microwave heating coil means on the base and extending in a direction opposite to the preheater means containing a tubing susceptible to the passage of microwave energy from the microwave guide means to permit the heating of the preheated fluid passing through the tubing to a selected temperature of greater than 60° C., the microwave heating coil means arranged and constructed to be inserted and positioned in the opening of the housing and within the microwave energy field of the microwave guide means; and iii) cooler means on the base and containing tubing therein to receive the microwave heated fluid and to cool rapidly the microwave heated fluid to a lower temperature of less than about 40° C. at a total heating, holding and cooling time of less than about 1 second; and h) tubing means to connect the feed source means, the pump means, the cartridge means and the collection means to permit the pumped passage of the fluid to be treated from the feed source through the cartridge means and to the collection means.

2. The system of claim 1 wherein the microwave heating coil comprises a plurality of loops of a flexible plastic tubing on a plastic coil retaining means to retain the plastic tubing in a substantially parallel, uniform, side-by-side coiled array of plastic tubing in the microwave coil means.

3. The system of claim 2 wherein the plastic coil retaining means comprises, extending from the base and a downwardly extending plastic holder having a plurality of spaced apart holes therein with the tubing extended through the holes in a positioned, arrayed, coiled fashion and wherein the tubing is plastic.

4. The system of claim 3 wherein the plastic coil retaining means comprises a plurality of aligned, spaced apart holes in an upper and in a lower section of the plastic holder for the sequential threading of the plastic coil therethrough.

5. The system of claim 4 wherein the plastic tubing comprises an microwave and infrared transparent plastic tubing.

6. The system of claim 1 wherein the preheater means and the cooler means both comprise metal tubing coiled within an interior housing, an outlet of the metal tubing of the preheater means and an inlet of the metal tubing of the cooler means secured to an inlet and an outlet respectively of the plastic tubing of the microwave coil means.

7. The system of claim 6 wherein the preheater means comprises an inlet for the introduction and an outlet for the withdrawal of water to preheat the fluid, and the cooler means comprises an inlet for the introduction and an outlet for the withdrawal of water to cool the microwave-heated fluid.

8. The system of claim 7 wherein the preheater and cooler means comprise a transparent plastic housing each housing positioned on the upper surface of the base with the plastic microwave coil retaining means extending downwardly from the base, and arranged and constructed to be positioned in an opening of the housing and within the microwave energy field of the microwave guide means.

9. The system of claim 1 wherein the cartridge means provides for the heating to a temperature greater than about 60° C. of a heat-sensitive fluid in a time of less than about 200 milliseconds and the cooling of the heat-treated fluid to a temperature of less than about 40° C. in a time of less than about 0.5 seconds.

10. The system of claim 1 wherein the tubing in the microwave heating coil means provides for the passage of infrared energy and which system includes a non-invasive fiber optic infrared sensor means to measure an inlet and an outlet temperature of the fluid into and out of the microwave heating coil means.

11. The system of claim 10 wherein the fiber optics infrared sensor means comprises a plurality of optical fibers arranged as a cable, the fiber optic cable adjacent an external surface of the infrared transparent plastic tubing at an inlet and at an outlet of the microwave heating coil means and an IR sensor in communication with the fiber optic cable to permit the IR sensor to measure the inlet and outlet temperatures of the heat-sensitive fluid in the microwave heating coil and means to communicate the measured temperatures to the electronic control means.

12. The system of claim 1 wherein the feed source means comprises a blood plasma or serum tissue media or other heat-sensitive fluid containing a pathogenic agent.

13. The system of claim 1 wherein the tubing in the preheater and cooler means comprises a stainless steel metal tubing with screw threads at one end thereof and wherein the tubing in the microwave heating coil means is plastic and is threadably turned into the threaded end of the metal tubing at the outlet of the preheater means and at the inlet end of the cooler means.

14. The system of claim 1 which includes a variable hold time means to extend or shorten the length of tubing between the microwave heating coil means and the cooler means thereby providing for adjustment of a holding time at which the fluid is held at a selected temperature.

15. The system of claim 14 which includes:
a) a mounting bracket on the base and secured to the cooler means; and
b) threaded means connected to the mounting bracket means to permit the vertical movement of the cooler means on the base to adjust the length of tubing outside of and between the microwave heating coil means and the cooler means, thereby providing for adjustment in the holding time of the fluid at the selected temperature.

16. The system of claim 15 wherein the microwave heating coil means includes a grooved, rotatable spool to hold a plurality of tubing coils to permit the adjustment in the length of the microwave-susceptible tubing.

17. A cartridge for use with a high temperature, short time microwave heating and cooling system, having a microwave heating guide within a housing having an opening to provide a microwave heating energy field within the opening and which cartridge comprises in combination:
a) a base;
b) preheater means on the base to preheat a heat-sensitive fluid to a selected preheated temperature;
c) microwave heating coil means which includes downwardly extending from the base, a microwave coil retaining means with a plurality of coils of plastic tubing on the coil retaining means, the tubing connected to the preheater means, the microwave coil means arranged and constructed to be placed within said opening of the housing and positioned in the microwave heating energy field and to be removed from said opening; and d) cooler means on the base for the cooling of the heated, heat-sensitive fluid from the microwave heating coil means to a selected cooling temperature.

18. The cartridge of claim 17 wherein the microwave heating coil means comprises a coil retaining means secured to a lower surface of the base and which includes a plurality of holes with a plastic tubing through the holes to retain the plastic tubing in the heating coil means in a substantially side-by-side, uniform, looped coil arrangement.

19. The cartridge of claim 17 wherein the microwave heating coil means includes a microwave coil retaining means composed of a plastic material having a plurality of aligned holes in an upper and a lower section and wherein the plastic tubing is sequentially passed through the aligned holes in the upper and lower sections to form a plurality of substantially uniform, side-by-side plastic tubing coils.

20. The cartridge of claim 17 wherein the preheater means and the cooler means each include a plurality of coiled metal tubing therein, an outlet of the metal tubing in the preheating means and an inlet of the metal tubing in the cooler means threaded and connected to an inlet and outlet respectively of the plastic tubing of the microwave heating coil means.

21. The cartridge of claim 17 wherein the plastic tubing employed in the microwave heating coil means comprises a transparent plastic tubing arranged and constructed for use with an infrared, fiber optic, temperature sensing means.

22. The cartridge of claim 17 wherein the preheater means includes an inlet and an outlet for the introduction and withdrawal of water to preheat the heat-sensitive fluid, and the cooler means includes an inlet and an outlet for the introduction and withdrawal of water for the cooling of the heated heat-sensitive fluid.

23. A high temperature, short time microwave heating system which includes a microwave wave guide, a microwave power source for the microwave wave guide and which includes the cartridge of claim 17 positioned in the microwave heating field of the microwave heating guide for the heating and cooling of heat-sensitive fluid.

24. The cartridge of claim 17 wherein the preheater means and the cooler means comprise a transparent plastic housing, each with an inlet and an outlet for the introduction and withdrawal of water, and which includes a plurality of metal coils therein to provide for the preheating and the cooling of the microwave heated, heat-sensitive fluid, and an outlet of the metal coil of the preheater means, and an inlet of the metal coil of the cooler means connected to the plastic tubing of the microwave heating coil means.

25. In a method for the rapid, high temperature, short time microwave heating of a heat-sensitive fluid having an organism or pathogenic agent which method comprises:

a) heating the fluid within a plastic tubing in a microwave energy field within a housing having an opening to a selected high temperature of greater than 60° C. to reduce or inactivate the organism or pathogenic agent, the heating, without substantial alteration of other desirable properties of the fluid the heating carried out in less than about 1.0 second;

b) holding the heated fluid for a selected time and at a selected temperature;

c) cooling the heated fluid to a temperature of less than about 40° C. in a period of less than about one second; and d) recovering the heated, cooled fluid, wherein the improvement comprises:

positioning a disposable cartridge means having a plastic, microwave heating coil means containing a plurality of substantially uniform, aligned, spaced apart coils of the plastic tubing within the microwave energy field, the plastic tubing retained in a coiled arrangement by a plastic coil holder which holder is easily inserted in and removed from the microwave heating field.

26. The method of claim 25 which includes providing a disposable cartridge means which includes a base having on an upper surface a preheater means to preheat the fluid, and a cooler means, the microwave heating coil means extending downwardly from the lower surface of the base and positioning the microwave heating coil means in the microwave energy field.

27. The method of claim 25 which includes retaining the plastic tubing of the microwave heating coil means in an arrayed coil form by a plurality of holes in the holder.

28. The method of claim 25 which includes securing each end of the plastic tubing to a threaded metal tubing outlet and a threaded metal tubing inlet respectively of a preheater means to preheat the fluid and a cooler means to cool the fluid.

29. The method of claim 25 which includes employing infrared transmissible plastic tubing and sensing the temperature of an inlet and an outlet of the plastic tubing by employing a fiber optic cable and an infrared sensor connected to the fiber optic cable, the fiber optic cable placed in a temperature sensing position adjacent the outside of the plastic tubing.

30. The method of claim 25 which includes varying the holding time at which the fluid is held at the selected temperature from about 0.25 milliseconds to 500.0 milliseconds.

31. The method of claim 25 which includes varying the length of plastic tubing between the heating of the fluid in the microwave energy field and the cooling of the fluid to adjust the holding time of the fluid.

32. The method of claim 25 which includes preheating the heat-sensitive fluid prior to heating the heat-sensitive fluid.

33. The method of claim 25 which includes employing transparent plastic tubing and indirectly, non-invasively sensing the temperature of the heat-sensitive fluid in the plastic tubing the an IR sensor means at an inlet and an outlet of the plastic tubing of the mcrowave heating coil means.

34. The method of claim 33 which includes IR sensing at an inlet temperature over a range of about 45° C. to 65° C. and IR sensing at an outlet temperature over a range of about 70° C. to 110° C.

* * * * *

UNITED STATES PATENT AND TRADEMARK OFFICE
CERTIFICATE OF CORRECTION

PATENT NO. : 5,389,335

DATED : February 14, 1995

INVENTOR(S) : Stanley E. Charm et al

It is certified that error appears in the above-identified patent and that said Letters Patent is hereby corrected as shown below:

```
Column 9, Claim 3:
Line 31, after "comprises", please insert --a downwardly
                              extending plastic holder--;
Line 32, before"having" , please delete "a downwardly
                              extending plastic holder".
```

Signed and Sealed this

Twenty-third Day of May, 1995

Attest:

BRUCE LEHMAN

Attesting Officer

Commissioner of Patents and Trademarks